US009609920B2

(12) United States Patent
Beuther et al.

(10) Patent No.: US 9,609,920 B2
(45) Date of Patent: Apr. 4, 2017

(54) PROCESS FOR MODIFYING A HOOK PROFILE OF A FASTENING COMPONENT AND A FASTENING COMPONENT HAVING HOOKS WITH A MODIFIED PROFILE (71) Applicant: Kimberly-Clark Worldwide, Inc., Neenah, WI (US)

(72) Inventors: Paul Douglas Beuther, Neenah, WI (US); David John Enz, Neenah, WI (US); Devin Charles McElrath, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 410 days.

(21) Appl. No.: 14/136,073

(22) Filed: Dec. 20, 2013

(65) Prior Publication Data
US 2015/0073377 A1 Mar. 12, 2015

Related U.S. Application Data (60) Provisional application No. 61/874,665, filed on Sep. 6, 2013.

(51) Int. Cl.
A44B 18/00 (2006.01)
A61F 13/62 (2006.01)

(52) U.S. Cl.
CPC ...... A44B 18/0015 (2013.01); A44B 18/0019 (2013.01); A61F 13/625 (2013.01); Y10T 29/49716 (2015.01)

(58) Field of Classification Search
CPC ............. A44B 18/0015; A44B 18/0019; A61F 13/625; Y10T 29/49716
See application file for complete search history.

(56) References Cited

U.S. PATENT DOCUMENTS 3,192,589 A 7/1965 Pearson
3,320,649 A 5/1967 Naimer
(Continued)

FOREIGN PATENT DOCUMENTS

EP 0381087 A1 8/1990
WO 0018268 A1 4/2000

OTHER PUBLICATIONS

Notification of Transmittal of the International Search Report and the Written Opinion of the International Searching Authority for International Application No. PCT/IB2014/063940, dated Mar. 16, 2015; 9 pages.

Primary Examiner — Galen Hauth
(74) Attorney, Agent, or Firm — Armstrong Teasdale LLP (57) ABSTRACT A method of modifying a male fastener of a fastening system includes feeding a web having a base substrate and a male fastening material to a modifying member having an outer surface. The male fastening material has a plurality of male fasteners with a first, unmodified profile. The profile of at least some of the plurality of male fasteners of the male fastening material are modified by engagement of the plurality of male fastener with the outer surface of the modifying member and by causing the plurality of male fasteners to slip along the outer surface of the modifying member. A modified male fastening material includes a plurality of male fasteners modified from a first profile to a second, different profile by passing the male fastening material over the outer surface of the modifying member.

13 Claims, 8 Drawing Sheets (56) References Cited

U.S. PATENT DOCUMENTS

| | | |
|---|---|---|
| 3,607,995 A | 9/1971 | Chiba |
| 3,718,725 A | 2/1973 | Hamano |
| 4,056,593 A | 11/1977 | De Navas Albareda |
| 4,454,183 A | 6/1984 | Wollman |
| 4,770,917 A | 9/1988 | Tochacek et al. |
| 4,775,310 A | 10/1988 | Fischer |
| 5,058,247 A | 10/1991 | Thomas et al. |
| 5,116,563 A | 5/1992 | Thomas et al. |
| 5,392,498 A | 2/1995 | Goulait et al. |
| 5,397,317 A | 3/1995 | Thomas |
| 5,441,687 A | 8/1995 | Murasaki et al. |
| 5,512,234 A | 4/1996 | Takizawa et al. |
| 5,565,255 A | 10/1996 | Young et al. |
| 5,586,371 A | 12/1996 | Thomas |
| 5,749,129 A | 5/1998 | Murasaki et al. |
| 5,781,969 A | 7/1998 | Akeno et al. |
| 5,868,987 A | 2/1999 | Kampfer et al. |
| 6,039,911 A | 3/2000 | Miller et al. |
| 6,054,091 A | 4/2000 | Miller et al. |
| 6,132,660 A | 10/2000 | Kampfer |
| H001952 H | 3/2001 | Reed et al. |
| 6,280,670 B1 | 8/2001 | Buzzell et al. |
| 6,494,244 B2 | 12/2002 | Parrish et al. |
| 2001/0000365 A1 | 4/2001 | Provost et al. |
| 2001/0022409 A1 | 9/2001 | Parellada et al. |
| 2003/0080453 A1 | 5/2003 | Bay et al. |
| 2004/0088835 A1 | 5/2004 | Tachauer et al. |
| 2005/0039313 A1 | 2/2005 | Melbye et al. |
| 2005/0206030 A1 | 9/2005 | Clune et al. |
| 2005/0230056 A1 | 10/2005 | Meyer et al. |
| 2006/0266466 A1 | 11/2006 | Meyer |
| 2009/0294044 A1 | 12/2009 | Gill et al. |
| 2012/0047695 A1* | 3/2012 | Picot .................. A44B 18/0065 24/449 |

* cited by examiner

Figure 10:
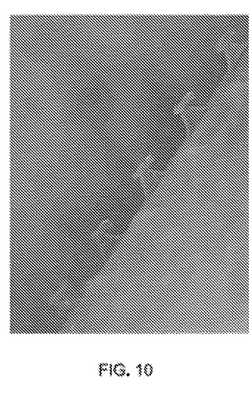
FIGS. 10-12 are photographs of a modified hook profile of a hook fastening material.
Figure 11:
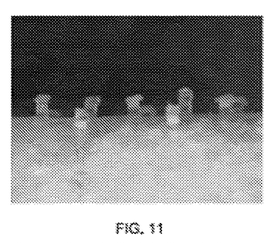
Figure 12:
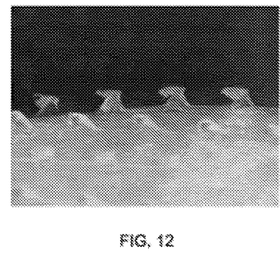

Figures 10-12, which are presented below, are photographs of the modified hook profile of the hook fastening material. As mentioned above, Figures 6 and 4 are line drawings illustrating the unmodified hook profile of the hook fastening material.

PROCESS FOR MODIFYING A HOOK PROFILE OF A FASTENING COMPONENT AND A FASTENING COMPONENT HAVING HOOKS WITH A MODIFIED PROFILE

CROSS-REFERENCE TO RELATED APPLICATION

This application claims the benefit of U.S. Provisional Application No. 61/874,665 filed Sep. 6, 2013, which is incorporated herein by reference in its entirety.

BACKGROUND

The present disclosure relates generally to a process for modifying a hook profile of a fastening component and a fastening component having hooks with a modified profile. More particularly, some aspects of the disclosure relate to using an anvil roll, anvil-roll plate, and/or a slip-and-cut system to modify a hook profile of a fastening component.

Many absorbent articles intended for personal wear, such as diapers, training pants, feminine hygiene products, adult incontinence products, bandages, medical garments, and the like have been manufactured by processes wherein discrete parts or segments of the article are deposited on a continuously moving product web. In such processes, a vacuum slip roll, anvil roll, or the like may be used when cutting, transporting, and transferring the segment to the moving product web. For example, a known slip-and-cut manufacturing process uses a vacuum drum rotating at a speed faster than an incoming web from which the segment is to be cut. The incoming web thus slips on the drum surface until a cut-off knife cuts a correct length of the web thereby forming the segment. The cut-off knife may be mounted on a cutting roll which cuts the segment from the incoming web when the knife comes into contact with the rotating vacuum drum. The cut segment is held to the surface of the drum by a vacuum drawn through holes provided in the drum. The segment is held and transported on the drum to a transfer point where the segment is transferred to the continuously moving product web forming at least a portion of the absorbent article.

In some applications, the incoming web (i.e., the web from which the discrete segments are to be cut) may comprise fastening components ultimately used to secure the absorbent article about a user. For example, the incoming web may comprise a base substrate with one or more fastening components extruded or otherwise disposed on the base substrates. The one or more fastening components may comprise any suitable material used to fasten the absorbent article about a wearer, such as a hook material. However, the profiles of the hooks provided on known hook materials may be inadequate to securely hold the absorbent article about a wearer. For example, and particularly when the absorbent article is an infant diaper or the like, the hook profile of known hook materials may be inadequate to securely hold the absorbent article about the wearer when the infant crawls, walks, runs, bends, etc.

Thus, for some applications it may be desirable to provide a complex hook profile such that the fastening components provide a more secure engagement with an associated mating fastening component (e.g., a loop material). However, in order to provide such a complex hook profile, different (and more complex) manufacturing processes may need to be used when forming the hooks and/or known hook materials may need to undergo additional manufacturing steps before the hook material is supplied to the vacuum drum of the slip-and-cut system. This may lead to an undesirable increase in time and expense when manufacturing an absorbent article.

In other applications it may be desirable to provide a complex hook profile such that the fastening components provide a less secure engagement with an associated mating fastening component (e.g., a loop material). However, in order to provide such a complex hook profile, different (and more complex) manufacturing processes may need to be used when forming the hooks and/or known hook materials may need to undergo additional manufacturing steps before the hook material is supplied to the vacuum drum of the slip-and-cut system. This may lead to an undesirable increase in time and expense when manufacturing an absorbent article.

Thus, there remains a need for a process to manufacture a complex hook profile without adding time, expense, and/or manufacturing steps to current slip-and-cut systems.

BRIEF DESCRIPTION

In one aspect, a method of modifying a male fastener of a fastening system generally comprises feeding a web comprising a base substrate and a male fastening material to a modifying member having an outer surface. The male fastening material comprises a plurality of male fasteners having a first, unmodified profile. A force is applied to the web to facilitate contact between at least some of the plurality of male fasteners and the outer surface of the modifying member. The profile of at least some of the plurality of male fasteners of the male fastening material is modified by causing the plurality of male fasteners to slip along the outer surface of the modifying member.

In another aspect, a method of modifying a hook fastener of a hook and loop fastening system generally comprises rotating a roll such that the roll has a surface speed. The roll has an inner surface, an outer surface, and a plurality of vacuum holes extending between the inner and outer surfaces. A web is fed to the roll at a speed slower than the surface speed of the roll. The web comprises a base substrate and a hook fastening material. The hook fastening material comprises a plurality of hooks having a first, unmodified profile when fed. A vacuum is applied to the roll. The vacuum is in fluid communication with the plurality of vacuum holes such that at least the hook fastening material of the web is drawn against the outer surface of the roll. The web is allowed to slips along the outer surface of the roll to modify the profile of the plurality of hooks of the hook fastening material.

In still another aspect, a method of modifying a male fastener of a fastening system generally comprises feeding a web comprising a base substrate and a male fastening material to a modifying member having an outer surface. The male fastening material comprises a plurality of male fasteners having a first, unmodified profile. The profile of at least some of the plurality of male fasteners of the male fastening material is modified by pneumatically engaging the plurality of male fasteners with the outer surface of the modifying member and causing the plurality of male fasteners to slip along the outer surface of the modifying member.

DETAILED DESCRIPTION OF THE DRAWINGS

Figure 1:
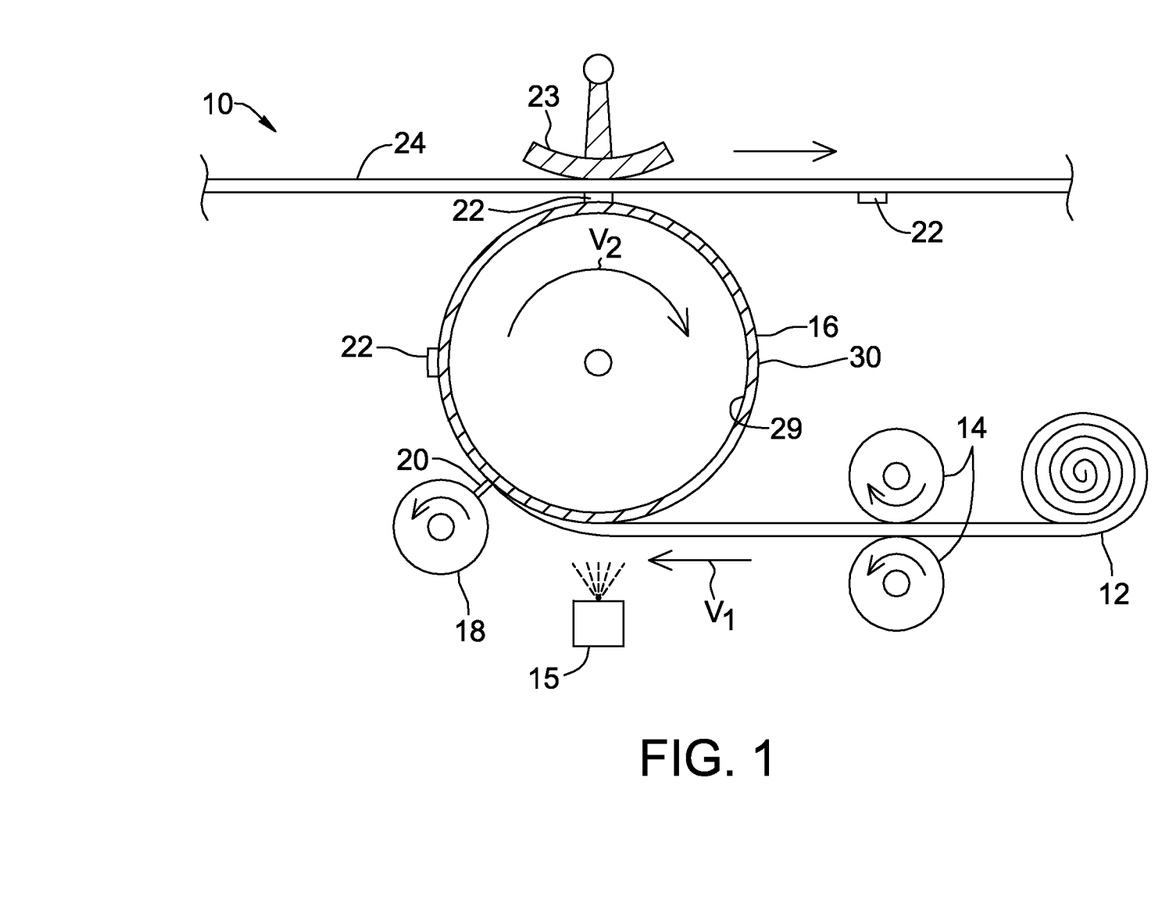
FIG. 1 is a side view of a slip-and-cut system according to one embodiment of the disclosure.

Turning now to the drawings, FIG. 1 illustrates a suitable slip-and-cut system, indicated generally at 10, used to form absorbent articles according to one embodiment of the disclosure. The absorbent articles may be, e.g., diapers, training pants, feminine hygiene products, adult incontinence products, bandages, medical garments, and the like. The slip-and-cut system 10 may be used to deposit a discrete part or segment 22 on a continuously moving product web 24. Specifically, an incoming web 12 may be fed to an anvil roll 16 (broadly, a "modifying member") via a web feeding assembly such as, e.g., one or more drive rollers 14. In the illustrated embodiment, a suitable adhesive is applied to the web 12 at an adhesive station 15 prior to or upon reaching the anvil roll 16. It is understood that the adhesive station 15 could be positioned at different location in the system 10. It is also understood that in other suitable embodiments the adhesive station 15 can be omitted.

Figure 3:
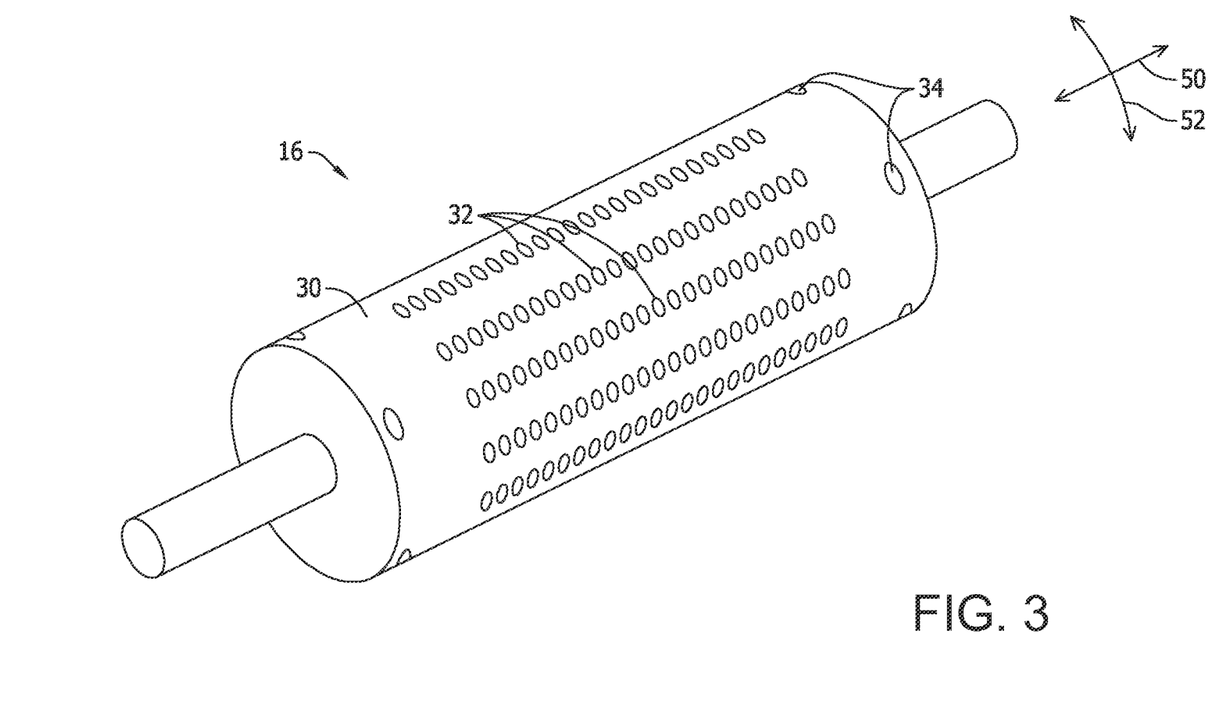
FIG. 3 is a perspective of one suitable embodiment of an anvil roll for use in the slip-and-cut system of FIG. 1.

In the illustrated embodiment, the anvil roll 16 is a vacuum roll formed as a tubular drum having an inner surface 29, and outer surface 30, and one or more vacuum holes 32 extending between the inner surface and the outer surface (FIG. 3). The anvil roll 16 may internally contain or otherwise be connected to a suitable vacuum source (such as, e.g., a vacuum pump, a vacuum chamber, etc., not shown) which is capable of selectively applying a vacuum pressure (i.e., negative pressure) through the one or more vacuum holes 32 such that materials provided to the outer surface 30 of the anvil roll are generally drawn to and secured against the outer surface. In some embodiments, the vacuum source may be capable of applying a vacuum in the range of 1 to 20 inches of water, and more preferably in the range of 3 to 10 inches of water, and even more preferably in the range of 4 to 7 inches of water.

In one suitable embodiment, the incoming web 12 is fed to the anvil roll 16 at a slower linear speed (as indicated by $V_1$ in FIG. 1) than the surface speed of the anvil roll (as indicated by $V_2$ in FIG. 1). In other words, the surface speed of the anvil roll 16 is greater than the speed at which incoming web 12 is fed to the anvil roll. As a result, the leading edge of incoming web 12 engages and slips against the outer surface 30 of the anvil roll 16. It is understood that the incoming web 12 can be fed to the anvil roll 16 at any suitable rate. For example, in one suitable embodiment, the incoming web 12 is fed to the anvil roll 16 at a rate between about ½ and about 1/20 the surface speed of the anvil roll. In other words, the surface speed of the anvil roll 16 is between about twice and about twenty times greater than the speed at which the incoming web 12 is fed to the anvil roll. In one preferred embodiment, the incoming web 12 is fed to the anvil roll 16 at a rate about 1/10 the surface speed of the anvil roll. In other words, the surface speed of the anvil roll is ten times greater than the speed at which the incoming web is fed to the anvil roll.

The slip-and-cut system 10 illustrated in FIG. 1 further comprises a knife roll 18 comprising one or more knife edges 20. The knife edge 20 may be oriented in a longitudinal direction 50 on the knife roll 18 (i.e., a direction substantially parallel to a center axis of the knife roll and the anvil roll 16) and may be configured to cut material provided on the surface 30 of the anvil roll when the knife edge comes in contact with the outer surface of the anvil roll. Thus, when the incoming web 12 is fed to the anvil roll 16, the knife edge 20 will cut the incoming web when the knife edge comes into contact with the outer surface 30 of the anvil roll forming a discrete segment 22.

For example, in the depicted embodiment, the knife roll 18 comprises one knife edge 20 such that the slip-and-cut system 10 is configured to cut the incoming web 12 one time per rotation of the knife roll. That is, for each complete rotation of the knife roll 18, the knife edge will come into contact with the surface 30 of the anvil roll 16 one time, thus forming one segment 22 per rotation of the knife roll. In other embodiments, the knife roll 18 may comprise more than one knife edge 20 such that the slip-and-cut system 10 is configured to cut the incoming web 12 more than one time per rotation of the knife roll 18.

Once the segment 22 has been cut from the incoming web 12 by the knife edge 20, the segment will be transported at the surface speed of the anvil roll 16 to the continuously moving product web 24. That is, once cut from the incoming web 12, the segment 22 will be held against to the outer surface 30 of anvil roll 16 via the vacuum drawn through the vacuum holes 32 extending between the inner and outer surface of the anvil roll. The segment 22 will thus travel at the same surface speed as the anvil roll 16 until it reaches the product web 24, where it is deposited on the product web forming a portion of the absorbent article.

In the illustrated embodiment, each of the segments 22 is adhered to the moving product web 24. More specifically, the segment 22 having adhesive thereon and the moving product web 24 are directed through a nip defined by the anvil roll 16 and a stomper 23 (or other suitable device, e.g., a roll). It is understood that the segment 22 can bonded to the moving product web using any suitable bonding technique.

The combined product web 24 and segment 22 are then transported as an assembly for further processing (e.g., cutting into discrete absorbent articles, folding the absorbent articles, packaging the absorbent articles, etc.). In one suitable embodiment, the moving product web 24 is being fed at the rate substantially equal to the rate (i.e., the speed of the outer surface 30 of the anvil roll 16) at which the segment 22 is being delivered thereto.

Figure 2:
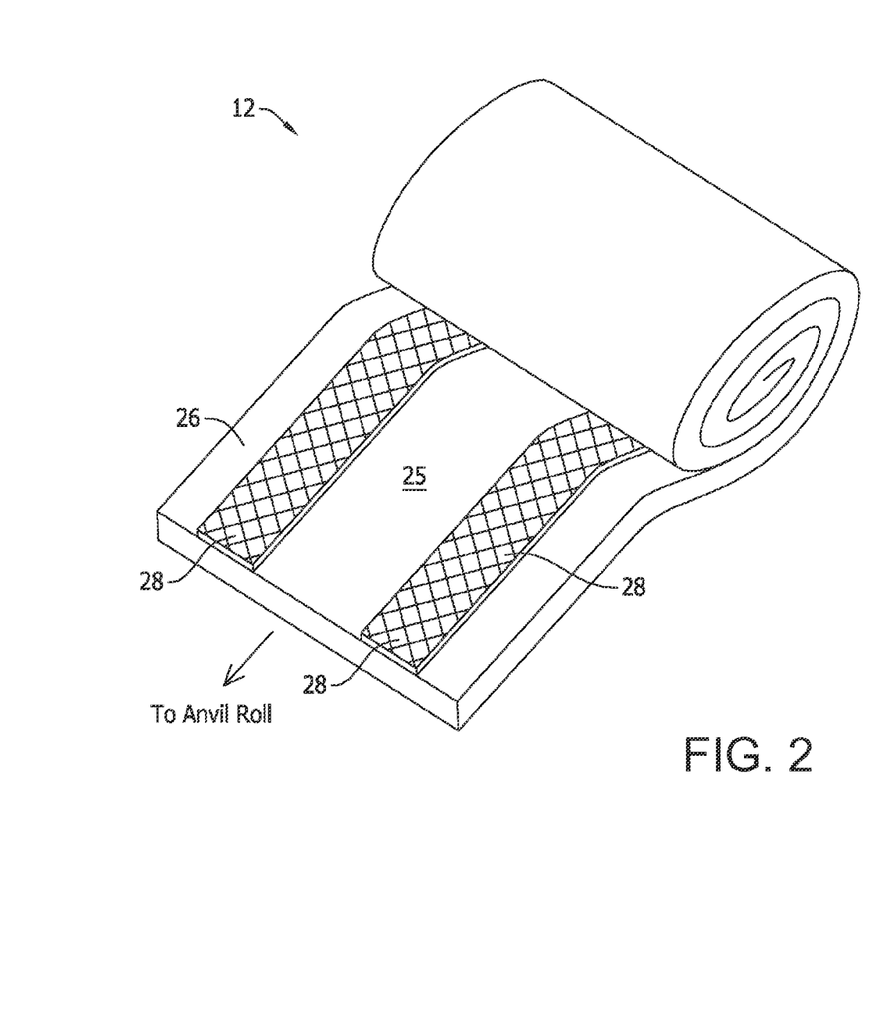
FIG. 2 is a perspective of an example web suitable for use in the slip-and-cut system of FIG. 1.

Turning now to FIG. 2, in one suitable embodiment, an anvil-facing surface 25 of the incoming web 12 (i.e., a surface which ultimately abuts the surface 30 of the anvil roll 16) may comprise a base substrate 26 with one or more strips of fastening material 28 extruded on or otherwise attached to the base substrate. In the depicted embodiment, the incoming web 12 comprises two strips of fastening material 28 extruded onto the base substrate 26, but, in other embodiments, the incoming web 12 may have any number of strips of fastening materials 28 and/or other components along an anvil-facing surface 25 of the incoming web. In some embodiments, the fastening material 28 may be, e.g., a male fastening material such as a hook fastening material, and more preferably, a polymer hook material, and even more preferably a low-density polyethylene hook material. In other embodiments, the fastening material 28 may be, e.g., a male fastening material formed from nylon, polypropylene, polypropylene-polyethylene blends, high-density polyethylene, linear-low-density polyethylene, or any other suitable material.

The fastening material 28 of the illustrated incoming web 12, and more particularly hooks 36 defining the fastening material of the incoming web (FIG. 4), may be further processed during interaction with the anvil roll 16 of the slip-and-cut system 10. This may be more readily understood with reference to FIGS. 3-7. First, FIG. 3 depicts one embodiment of an anvil roll 16 suitable for use in the slip-and-cut system 10 according to one embodiment of the disclosure. The anvil roll 16 comprises a plurality of vacuum holes 32 extending between the inner surface and the outer surface 30 of the anvil roll. The outer surface 30 of the anvil roll 16 may comprise additional apertures or the like, such as mounting holes 34 spaced along the outer edges of the anvil roll in a circumferential direction 52, without departing from the scope of this disclosure. In some embodiments, the anvil roll 16 may be constructed by applying an arcuate plate to the circumference of a vacuum drum which is secured using the mounting holes 34.

In the depicted embodiment, the vacuum holes 32 are aligned along the outer surface 30 of the anvil roll 16. That is, the vacuum holes 32 are aligned in rows in the longitudinal direction 50 along the surface 30 of the anvil roll 16, as well as aligned in columns in the circumferential direction 52 along the surface of the anvil roll. However, it should be appreciated that the embodiment depicted in FIG. 3 is merely illustrative and that, in other embodiments, the vacuum holes 32 may not be aligned in one or both directions and/or that certain regions of the outer surface 30 of the anvil roll 16 may comprise more or less vacuum holes without departing from the scope of this disclosure. Further, a vacuum pressure drawn through the vacuum holes 32 may vary along the longitudinal or circumferential directions 50, 52 of the anvil roll 16 such that different regions are subjected to different pressures. For example, a region of the anvil roll 16 which ultimately abuts the fastening material 28 may be subjected to a different vacuum pressure than a region of the anvil roll which ultimately abuts the base substrate 26. That is, the region of the anvil roll 16 which ultimately abuts the fastening material 28 may be subjected to a greater vacuum pressure or a lesser vacuum pressure than the region of the anvil roll which ultimately abuts the base substrate 26

During operation, the incoming web 12 is fed to the anvil roll 16, pneumatically engaged with the outer surface 30 of the anvil roll by the vacuum drawn through the vacuum holes 32, and slipped along the outer surface of the anvil roll until a segment 22 is cut free via the knife edge 20 provided on the knife roll 18. More particularly, the anvil-facing surface 25 of the incoming web 12 (and accordingly the fastening material 28) will slip along the outer surface 30 of the anvil roll 16 until the segment 22 is cut free. After cutting, the segment 22 will adhere to the outer surface 30 of the anvil roll via the vacuum pressure 30 drawn through the vacuum holes 32, where it will be transported downstream to the continuously moving product web 24. Thus, during transporting, the fastening material 28 will press against the outer surface 30 of the anvil roll 16.

In some embodiments, the incoming web 12, fastening material 28, anvil roll 16, and/or the slip-and-cut system 10 are configured such that a complex profile of the hooks 36 provided in the fastening material 28 may be formed when the incoming web slips on the surface 30 of the anvil roll and/or when the segment is transferred to the product web 24 via the anvil roll. It is understood that the complex profile of the hooks 36 can be influenced by one or more of friction, heat, dwell time, relative speed of the fastening material and the anvil roll and the force at which the fastening material contacts the anvil roll.

In one suitable embodiment, the anvil roll 16, and more broadly the slip-and-cut system 10, is free from a heat source. That is, no components of the slip-and-cut system 10 including the anvil roll 16 are heated using a heat source. Rather, the entire slip-and-cut system 10 of the illustrated embodiment is operated at or below ambient temperature. While heat is introduced into the system 10 by friction between the fastening material 28 and the surface 30 of the anvil roll 16 as the incoming web slips on the surface 30 of the anvil roll, airflow created by the vacuum being drawn through the vacuum holes 32 in the surface of the anvil roll quickly draws the heat out of the system and away from the fastening material being modified. Thus, the vacuum being drawn through the vacuum holes 32 effectively cools the slip-and-cut system 10 during operation.

It is contemplated that in other embodiments, the anvil roll 16 can be replaced with another suitable modifying member or modifying members. For example, the anvil roll 16 can be replaced with a modifying member in the form of a stationary arcuate plate over which the fastening material 28 is passed. In one suitable embodiment, the outer surface of the arcuate plate is configured to modify the profile of the fastening materials 28 as the fastening materials are moved across the outer surface.

Figure 4:
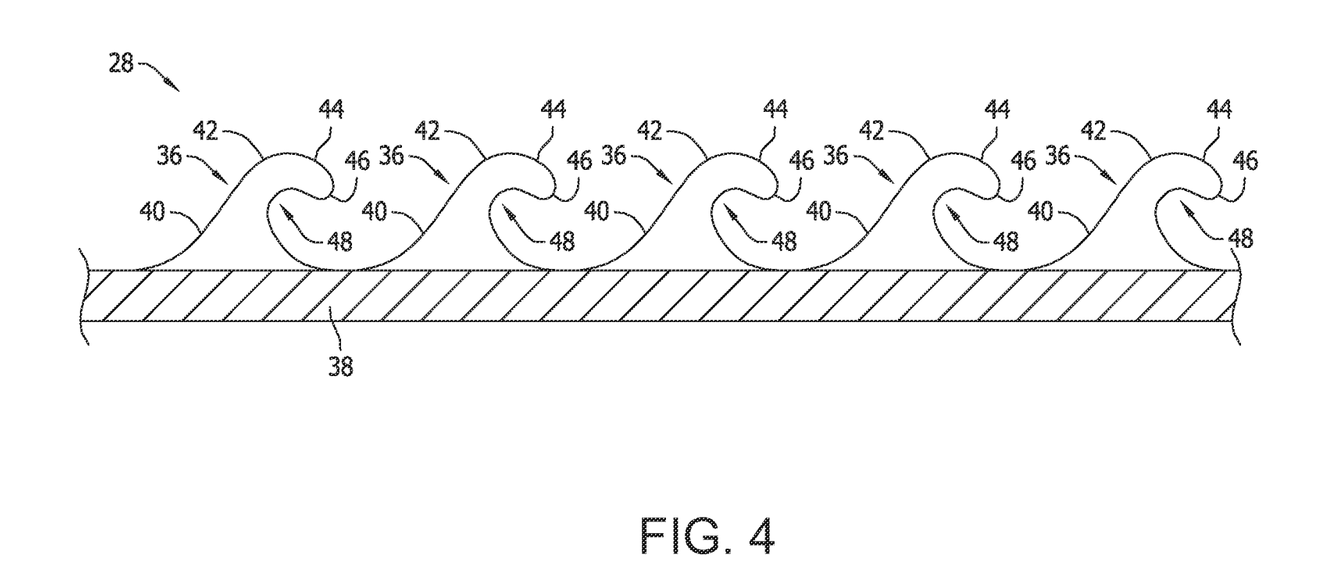
FIG. 4 is a side view of an unmodified hook profile of a hook fastening material provided on the web of FIG. 2.
Figure 8:
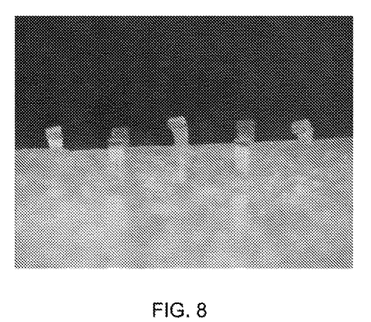
FIGS. 8 and 9 are photographs of an unmodified hook profile of a hook fastening material.
Figure 9:
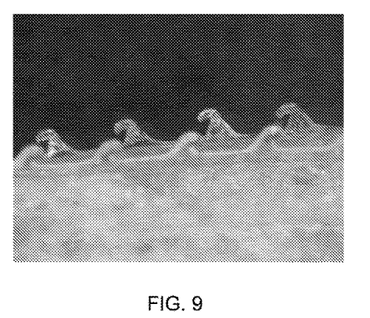

This may be more readily understood with reference to FIGS. 4-7. First, FIG. 4 depicts a side view of hooks 36 provided within the fastening material 28 of the incoming web 12 before being processed at the anvil roll 16 or other suitable modifying member (e.g., before being fed to the slip-and-cut system 10 by the one or more drive rollers 14 or the like as illustrated in FIG. 1). That is, the hooks 36 illustrated in FIG. 4 have an unmodified profile. FIGS. 8 and 9 are photographs of hooks having an unmodified profile. The fastening material 28 comprises a substrate 38 with a plurality of hooks 36 extruded or otherwise disposed on the substrate. In some embodiments, the substrate 38 may be attached to (e.g., bonded to, adhered to) the base substrate 26 of the incoming web 12. In other embodiments, the base substrate 26 of the incoming web 12 and the substrate 38 may be the same, with the hooks 36 thus being extruded directly or otherwise disposed on the base substrate.

Figure 5:
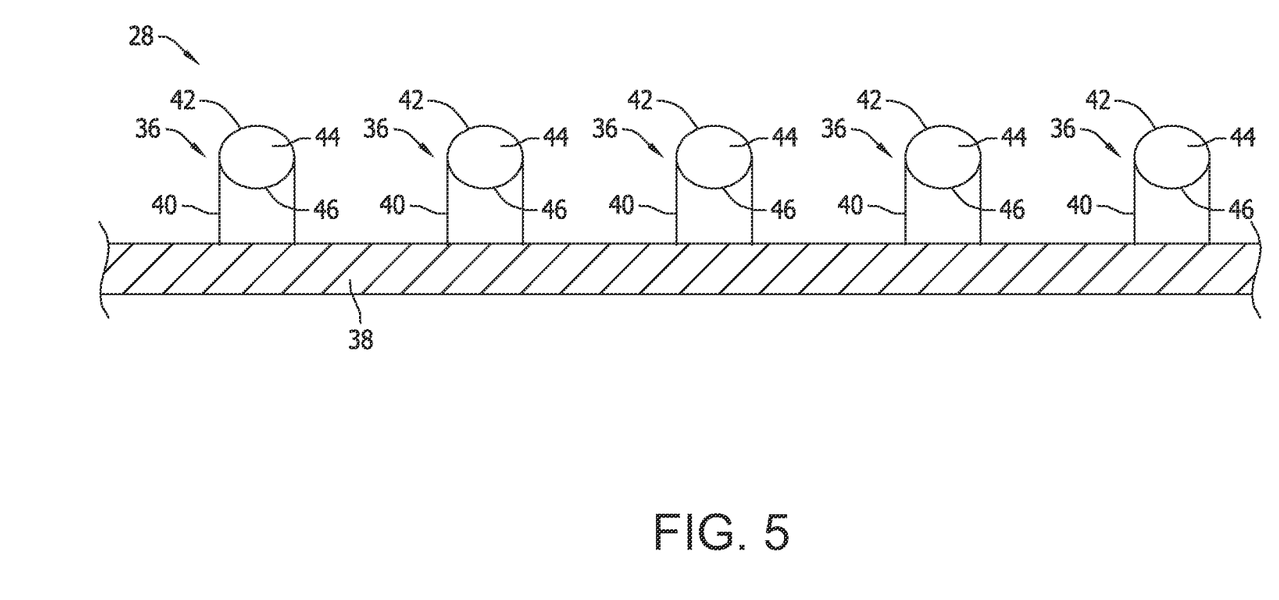
FIG. 5 is a front view of the hook profile of the hook fastening material of FIG. 4.

As illustrated in FIGS. 4 and 5, each hook 36 of the plurality of hooks comprises a stem 40 abutting the substrate 38 which extends upwardly from the substrate to a top 42 of the hook. In the depicted embodiment, each hook 36 also comprises a hook portion 44 extending down from the top 42 to a tip 46 overhanging the stem 40 such that a gap 48 is formed between the hook portion and the stem. As shown in FIG. 5, which illustrates a front view of the hooks 36, the hook portion 44 of each hook is generally the same width as the stem 40 of each hook. As will be appreciated that the hook 36 may be configured to engage a corresponding loop provided in a loop material (not shown) of a fastening system. In such embodiments, the hook portion 44 may engage the corresponding loop such that the loop is received in the gap 48 of the hook 36, securing the loop material to fastening material 28.

The hooks 36 may be formed to any desirable dimensions without departing from the scope of this disclosure. By way of an example, in one suitable embodiment, the hooks 36 may be formed as having a height (i.e., a vertical dimension extending from a point where the stem 40 attaches to the substrate 38 to the top 42 of the hook) of approximately 0.0076 inches. The hooks 36 may be formed as having a hook depth (i.e., a vertical dimension extending from the top 42 of the hook to the tip 46 of the hook) of approximately 0.0028 inches. And the hooks 36 may be formed as having a hook width (i.e., a horizontal dimension from the hook tip 46 to a leftmost edge of the stem 40 aligned with the hook tip) of approximately 0.0060 inches. Further, the fastening material 28 may be formed with any suitable hook 36 density (i.e., a number of hooks per unit area on the substrate 38). In one suitable embodiment, the fastening material 28 may be formed having a density of approximately 1000 to 3000 hooks per square inch, and more preferably 2000 to 2500 hooks per square inch, and even more preferably approximately 2300 hooks per square inch.

When fed to the anvil roll 16 of the slip-and-cut system 10 (or other suitable modifying member), the fastening material 28 will slip along the outer surface 30 with the hooks 36 facing the outer surface, and more particularly with the top 42 of each hook contacting the outer surface. Further, any portion of the hooks 36 (e.g., the stem 40, top 42, hook portion 44, tip 46, etc.) may engage one or more vacuum holes 32 when the fastening material 28 slips on the outer surface 30 of the anvil roll 16 seen in FIG. 1. When the segment 22 is cut from the incoming web 12 and transported to the product web 24 via the vacuum pressure drawn through the vacuum holes 32, the fastening material 28 will press against the outer surface 30 of the anvil roll, with the top 42 of each hook 36 abutting against the outer surface.

During this process, the profile of each hook 36 may be modified, forming a complex hook ultimately used in the fastening system of the absorbent article. More particularly, the friction force and pressure exerted on each hook 36 by the outer surface of the anvil roll 16 or other modifying member may cause the hook 36 to depress or otherwise deform, resulting in a complex (or modified) hook profile. In one suitable embodiment, the complex hook profile is formed by providing polymer hooks 36 to the anvil roll 16 under a suitable vacuum pressure.

Figure 6:
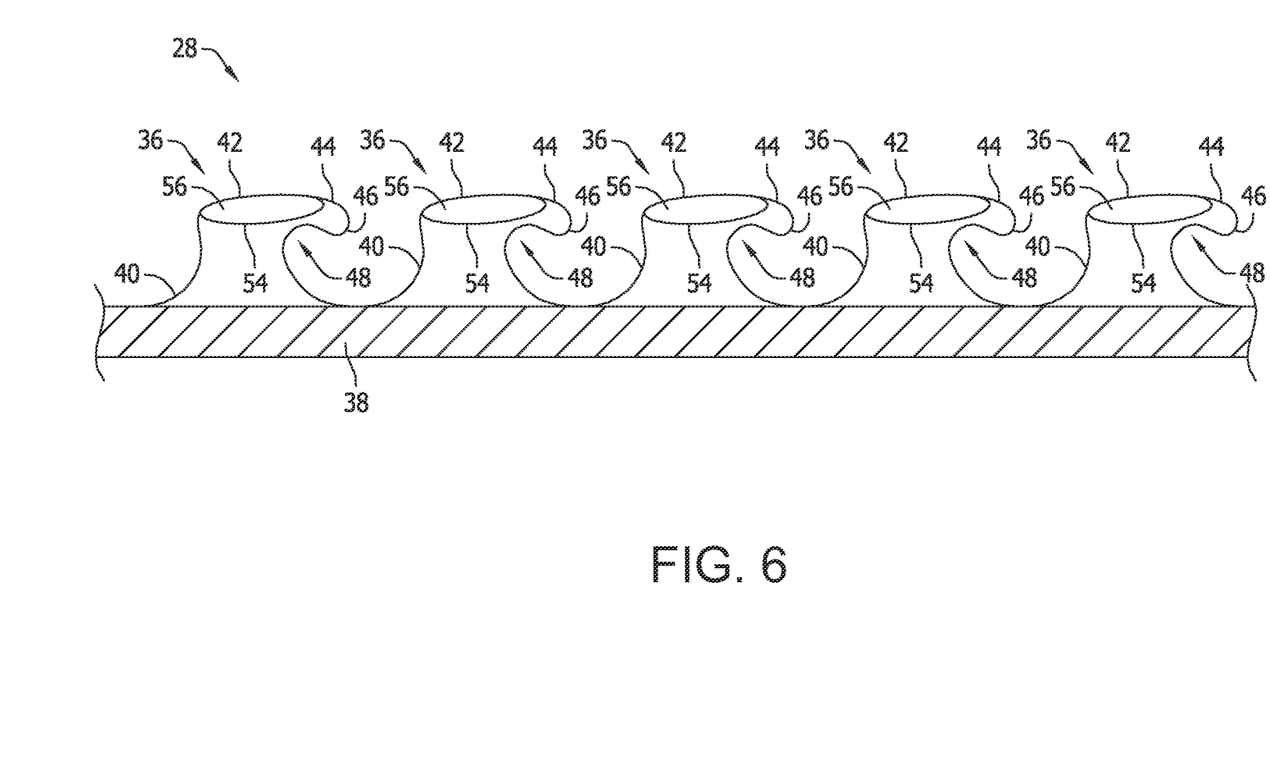
FIG. 6 is a side view of a modified hook profile of the hook fastening material of FIG. 4 following processing by the anvil roll of FIG. 3.
Figure 7:
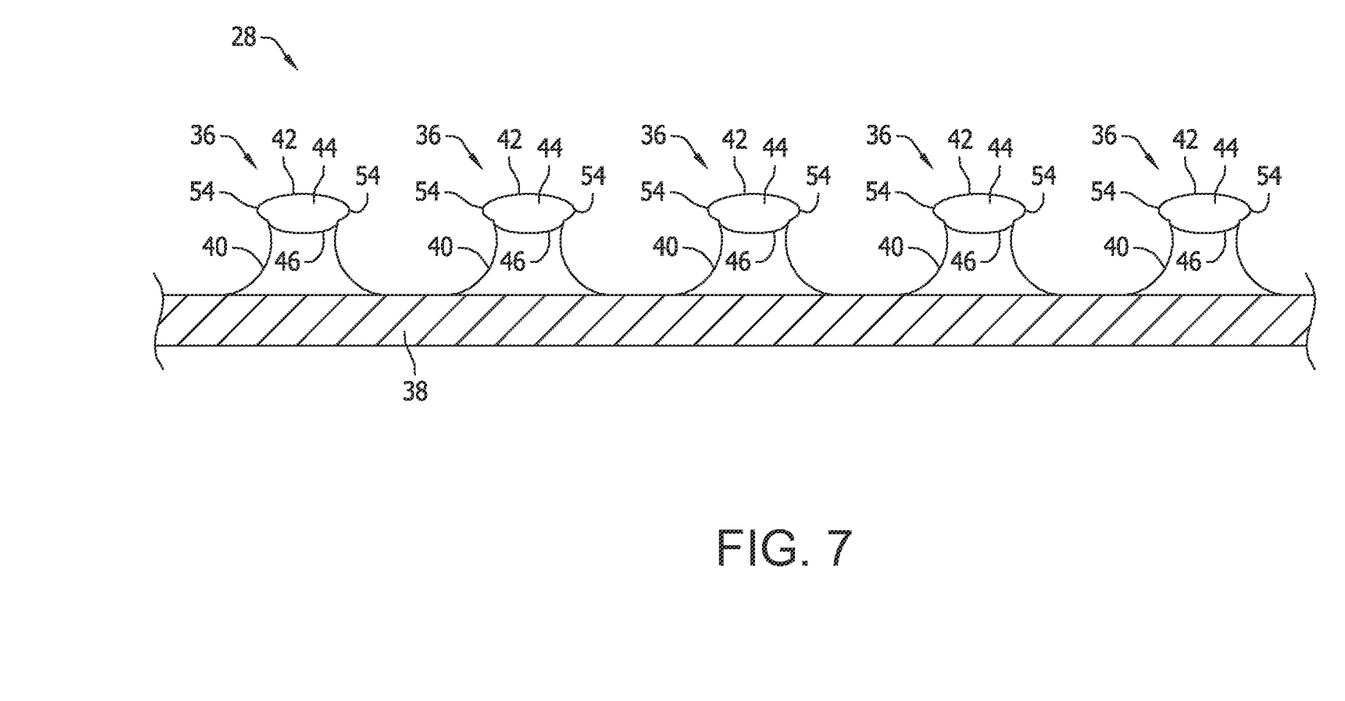
FIG. 7 is a front view of the modified hook profile of the hook fastening material of FIG. 6.

For example, FIGS. 6-7 illustrate a side view and a front view, respectively, of an example modified hook profile that may be formed following the slipping and/or transporting processes of the slip-and-cut system 10. FIGS. 10-12 are photographs of hooks having a modified profile. As illustrated in FIGS. 6-7, at least some of the hooks 36 are depressed, with the top 42 of the hook being flatter and closer to the tip 46 and gap 48 of the hook than the top was before the slipping and transporting processes. The hook may also comprise overhang 56 where a portion of the hook 36 extends over the stem 40 at a back of the hook (i.e., the left side of the hook as viewed in FIG. 6) and/or overhangs 54 where portions of the hook extend outwardly from the stem 40 of the hook when viewed from the front (FIG. 7). Thus, the illustrated modified hooks 36 are longer and wider as compared to the unmodified hooks.

The hooks 36 comprising complex profiles (FIGS. 6 and 7) may exhibit one or more benefits as compared to the hooks before being modified (FIGS. 4 and 5). For example, in addition the hook portion 44 engaging corresponding loop material, other portions of the hook 36 may engage the loop material forming a stronger or greater engagement. For example, one or more of the overhangs 54, 56 may engage the loop material in addition to the hook portion 44. Further, these increased engagement properties or the like may be provided without adding additional processes to the slip-and-cut system 10. For example, in one suitable embodiment, the hooks 36 are extruded onto the base substrate 26 of the incoming web 12 and constructed from a relatively pliable material (e.g., low-density polyethylene or other suitable polymer) such that the resulting complex profile is achieved during processing of the hooks. Accordingly, no additional equipment, processes, etc., are needed in order to form the hooks 36 with a modified profile which may have greater engagement properties than the unmodified hooks of FIGS. 4 and 5.

In some embodiments, by using the processes depicted and discussed herein, an overall reduction in cost and/or materials used to form hooks used in a fastening system of the absorbent article may be achieved. For example, in some embodiments the fastening material 28 extruded or otherwise disposed on the base substrate 26 may not comprise a hook shaped profile before being processed. For example, and returning to FIG. 4, in some embodiments the hooks may not comprise hook portion 44 before being fed to the slip-and cut system 10, but rather may only comprise the stem 40 portions. Such stem-only male fastening members may comprise the stem 40 which extends upwards to the top 42, but which has no portion extending from the top 42 and overhanging the stem 40 (unlike the hook portion 44 depicted in FIG. 4) prior to processing in the slip-and-cut system. In such embodiments, the stem-only male fastening members may not have very useful engagement properties prior to processing because the hooks do not comprise any projections, etc., to engage with a corresponding loop material when ultimately fastened about a wearer.

However, due to the less complex shape of the stem-only male fastening members, the stems may be constructed from less material and/or may be cheaper to manufacture than comparable hooks. Further, and particularly when the stem-only male fastening members are constructed of a relatively soft material such as low-density polyethylene or other suitable polymer, the hooks may be processed to form projections or the like such that the resulting hooks comprise sufficient engagement properties for the fastening system of the absorbent article. For example, during slipping along the surface 30 of the anvil roll 16 and/or transporting to the product web 42, the stem-only male fastening members may be compressed or otherwise deformed, forming projections which may ultimately engage with a loop material. For example, the processing (i.e., slipping and transporting) of the fastening material 28 may cause the stem-only male fastening members to form projections similar to the hook portion 44 depicted in FIGS. 4-7 and/or the overhangs 54, 56 depicted in FIGS. 6 and 7. As such, hooks or hook-like structures may be formed to have suitable engagement properties without requiring a complex and/or expensive manufacturing process of the fastening material.

It should be appreciated that the shape of the hooks 36 before the processing in the slip-and-cut system 10 or other suitable modifying system are not limited those specific shapes depicted and described above, but rather, in practice may be any suitable mechanical fastener having any desirable shape which is then processed as described forming a more complex hook profile. For example, in some embodiments the male fastening members may comprise, e.g., bulbs, mushrooms, arrowheads, balls on stems, stems, structures having stems that engage foam such as open cell foam or the like, etc. In any event, and particularly when constructed from, e.g., low-density polyethylene or the like, the male fastening members may be further processed in the slip-and-cut system 10 following manufacture of the incoming web 12, thus providing for increased fastening properties, reduced material usage, and/or reduced manufacturing expense.

In one suitable embodiment, the fastening material 28 and more specifically the hooks 36 have a flexural modulus between about 100,000 psi and about 150,000 psi; a tensile strength at yield between about 2,300 psi and about 3,500 psi; and/or a multiaxial impact between about 21 joules and about 33 joules. In one suitable example, the hooks have a flexural modulus of about 130,000 psi; a tensile strength at yield of about 2,900 psi; and multiaxial impact of about 27 joules. It is understood that the flexural modulus, tensile strength at yield, and multiaxial impact can be readily determined according to standard text methods including ASTM D790, ASTM D638, and ASTM D3763, respectively.

In one suitable embodiment, the fastening material 28 and more specifically the hooks 36 have a DSC Melting Point between about 135° C. and about 159° C.; a thermal conductivity between about 0.8 W/m/° K and about 1.2 W/m/° K; a coefficient of linear thermal expansion between about $6\times10^{-5}$ cm/(cm ° C.) and about $9\times10^{-5}$ cm/(cm ° C.); and/or a vicat softening temperature between about 143° C. and about 151° C. In one suitable example, the fastening material 28 and more specifically the hooks 36 have a DSC Melting Point of about 147° C.; a thermal conductivity of about 1.0 W/m/° K; a coefficient of linear thermal expansion of about $7.5\times10^{-5}$ cm/(cm ° C.); and a vicat softening temperature of about 147° C.

The slip-and-cut system 10 and any of the components and processes described herein may be used to apply a discrete segment 22 to a product web 24 to form portions of an absorbent article such as a diaper or the like, with the segment comprising fastening material 28 having hooks 36 with complex profiles thus resulting in greater engagement properties. For example, commonly owned U.S. patent application Ser. No. 13/953,364 entitled "Folded Absorbent Article with a Fastening System," Ser. No. 13/953,380 entitled "Absorbent Article Having a Fastening System," and Ser. No. 13/953,396 entitled "Absorbent Article Having a Fastening System With Low Stiffness," which were each filed on Jul. 29, 2013, and which are each incorporated herein by reference in its entirety, describe an absorbent article comprising a primary second fastening component and secondary first fastening component disposed on an outside cover of a diaper. Some embodiments of the slip-and-cut system 10 described herein may be used when manufacturing the diaper described in each referenced application in order to place the primary second fastening component and/or secondary first fastening component on the outside cover of the diaper.

For example, a web may be provided to the slip-and-cut system 10 which comprises a base substrate formed from the primary secondary fastening component material (e.g., a loop material) and two strips extruded onto or otherwise attached to the base substrate formed from the secondary first fastening component material (e.g., a hook material such as a polyethylene hook material). In such embodiments, when the web comprising the primary second fastening component and the secondary first fastening component is provided to the slip-and-cut system 10, the secondary first fastening component (e.g., polyethylene hook material) may abut and slip against the anvil roll 16, thus further processing the hooks forming a complex hook profile as discussed. Further, when a segment of the web comprising the primary second fastening component and the secondary first fastening component is cut from the rest of the web by the knife edge 20 and transported by the anvil roll 16 to a product web, the vacuum pressure applied to the segment through the vacuum holes 32 may further compress the hooks against the surface 30 of the anvil roll 16, thus further forming a complex profile having increased engagement properties or the like.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of modifying a male fastener of a fastening system, the method comprising:
feeding a web comprising a base substrate and a male fastening material to a modifying member having an outer surface with a plurality of holes, the male fastening material comprising a plurality of male fasteners having a first, unmodified profile;
applying a force to the web to facilitate contact between at least some of the plurality of male fasteners and the outer surface with the plurality of holes of the modifying member; and
modifying the profile of at least some of the plurality of male fasteners of the male fastening material by causing the plurality of male fasteners to slip along the outer surface with the plurality of holes of the modifying member.

2. The method of claim 1, wherein modifying the profile of at least some of the plurality of male fasteners of the male fastening material comprises causing the plurality of male fasteners to have greater widest dimension.

3. The method of claim 1, wherein modifying the profile of at least some of the plurality of male fasteners of the male fastening material comprises making a height of the plurality of male fasteners shorter.

4. The method of claim 1, wherein modifying the profile of at least some of the plurality of male fasteners of the male fastening material comprises making a length of the plurality of male fasteners greater.

5. The method of claim 1, wherein the plurality of male fasteners are adapted to engage a loop fastener.

6. The method of claim 4, wherein the plurality of male fasteners comprises at least one of hooks, bulbs, mushrooms, arrowheads, balls on stems, stems.

7. A method of modifying a male fastener of a fastening system, the method comprising:
feeding a web comprising a base substrate and a male fastening material to a modifying member having an outer surface, the male fastening material comprising a plurality of male fasteners having a first, unmodified profile;
applying a force to the web to facilitate contact between at least some of the plurality of male fasteners and the outer surface of the modifying member;
modifying the profile of at least some of the plurality of male fasteners of the male fastening material by causing the plurality of male fasteners to slip along the outer surface of the modifying member; and cutting a discrete segment from the web slipping on the outer surface of the modifying member using a knife roll.

8. The method of claim 7, wherein the modifying member is an anvil roll.

9. The method of claim 8, further comprising transporting the discrete segment via a vacuum pressure applied to the outer surface of the anvil roll by a vacuum source.

10. The method of claim 9, further comprising transferring the discrete segment to a product web.

11. A method of modifying a male fastener of a fastening system, the method comprising:
 feeding a web comprising a base substrate and a male fastening material to a modifying member having an outer surface, the male fastening material comprising a plurality of male fasteners having a first, unmodified profile; and
 modifying the profile of at least some of the plurality of male fasteners of the male fastening material by pneumatically engaging the plurality of male fasteners with the outer surface of the modifying member and causing the plurality of male fasteners to slip along the outer surface of the modifying member.

12. The method of claim 11, wherein modifying the profile of at least some of the plurality of male fasteners of the male fastening material by pneumatically engaging the plurality of male fastener with the outer surface of the modifying member comprises using a vacuum to draw at least some of the plurality of male fasteners against the outer surface of the modifying member.

13. The method of claim 11, wherein the modifying member is free from a heat source.

\* \* \* \* \*